United States Patent

[19]

Horner et al.

[11] Patent Number: 6,086,827
[45] Date of Patent: Jul. 11, 2000

[54] REACTION RECEPTACLE APPARATUS

[75] Inventors: Glenn A. Horner, Boulder, Colo.; Shirley J. Johnson, Del Mar, Calif.; Robert E. Schneider; Robert J. Smith, both of Louisville, Colo.; Gus Tseo, San Diego, Calif.

[73] Assignee: Gen-Probe Incorporated, San Diego, Calif.

[21] Appl. No.: 09/070,726

[22] Filed: May 1, 1998

Related U.S. Application Data

[60] Provisional application No. 60/046,800, May 2, 1997.

[51] Int. Cl.$^7$ ............................ B01L 3/00; G01N 35/00
[52] U.S. Cl. ............................ 422/102; 422/63; 422/65; 422/104; 206/438; 206/443; 436/47
[58] Field of Search ............................ 422/63, 65, 102, 422/103, 104; 436/43, 47; 206/438, 443

[56] References Cited

U.S. PATENT DOCUMENTS

| | | | |
|---|---|---|---|
| D. 273,807 | 5/1984 | Holen | D24/226 |
| D. 332,145 | 12/1992 | Wada et al. | D24/227 |
| D. 367,714 | 3/1996 | Pennicook | D24/223 |
| 3,350,946 | 11/1967 | Isreeli | 73/864.91 |
| 3,676,076 | 7/1972 | Grady | 422/100 |
| 3,684,453 | 8/1972 | Lartigue et al. | 422/102 |
| 3,785,773 | 1/1974 | Rohrbaugh | 422/102 |
| 4,287,155 | 9/1981 | Tersteeg et al. | 422/64 |
| 4,391,780 | 7/1983 | Boris | 422/102 |
| 4,478,094 | 10/1984 | Salomaa et al. | 73/863.32 |
| 4,577,760 | 3/1986 | Rainin et al. | 206/508 |
| 4,675,299 | 6/1987 | Witty et al. | 436/165 |
| 4,690,900 | 9/1987 | Kimmo et al. | 436/47 |
| 4,751,186 | 6/1988 | Baisch et al. | 436/47 |
| 4,824,641 | 4/1989 | Williams | 422/100 |
| 5,009,316 | 4/1991 | Klein | 206/443 |
| 5,039,615 | 8/1991 | Takahata | 436/44 |
| 5,240,678 | 8/1993 | Litsche | 422/64 |
| 5,260,028 | 11/1993 | Astle | 422/81 |
| 5,397,542 | 3/1995 | Nelms et al. | 422/104 |
| 5,456,887 | 10/1995 | Calvo et al. | 422/104 |
| 5,491,067 | 2/1996 | Setcavage et al. | 435/7.25 |
| 5,589,137 | 12/1996 | Markin et al. | 422/104 |
| 5,605,665 | 2/1997 | Clark et al. | 422/102 |
| 5,609,822 | 3/1997 | Carey et al. | 422/63 |
| 5,639,425 | 6/1997 | Komiyama et al. | 422/63 |
| 5,658,532 | 8/1997 | Kuosaki et al. | 422/64 |
| 5,665,558 | 9/1997 | Frame et al. | 435/7.25 |
| 5,665,562 | 9/1997 | Cook | 435/35 |
| 5,700,429 | 12/1997 | Buhler et al. | 422/104 |
| 5,849,247 | 12/1998 | Uzan et al. | 422/65 |
| 5,985,671 | 11/1999 | Leistner et al. | 436/49 |
| 6,010,911 | 1/2000 | Baugh et al. | 436/69 |

FOREIGN PATENT DOCUMENTS

| | | |
|---|---|---|
| 0 246 632 | 11/1987 | European Pat. Off. . |
| 0 467 301 | 1/1992 | European Pat. Off. . |
| 88/05541 | 7/1988 | WIPO ..................... 422/65 |
| 290018 | 11/1988 | WIPO ..................... 436/47 |

*Primary Examiner*—Mark Spisich
*Attorney, Agent, or Firm*—Charles B. Cappellari; Richard Wydeven

[57] ABSTRACT

A reaction receptacle apparatus includes one or more individual receptacles for containing chemical or biological substances. The one or more receptacles are arranged to be engaged by tubular elements of a substance transfer device for transferring substances into or out of the individual receptacles. Multiple receptacles are coupled to one another by a connecting rib structure that defines straight shoulders along opposite sides of the reaction receptacle apparatus, and the shoulders support the apparatus within reaction receptacle apparatus carrying structures. A contact-limiting element holding structure for holding contact-limiting elements, such as protective tips for tubular elements, is associated with each individual receptacle and holds a contact-limiting element in an operative orientation so as to be operatively engageable by the tubular element of the substance transfer device. A receptacle apparatus manipulating structure permits the reaction receptacle apparatus to be moved from one location to another by a robotic manipulating device, and an information panel presents a surface on which human and/or machine readable information may be placed.

39 Claims, 6 Drawing Sheets

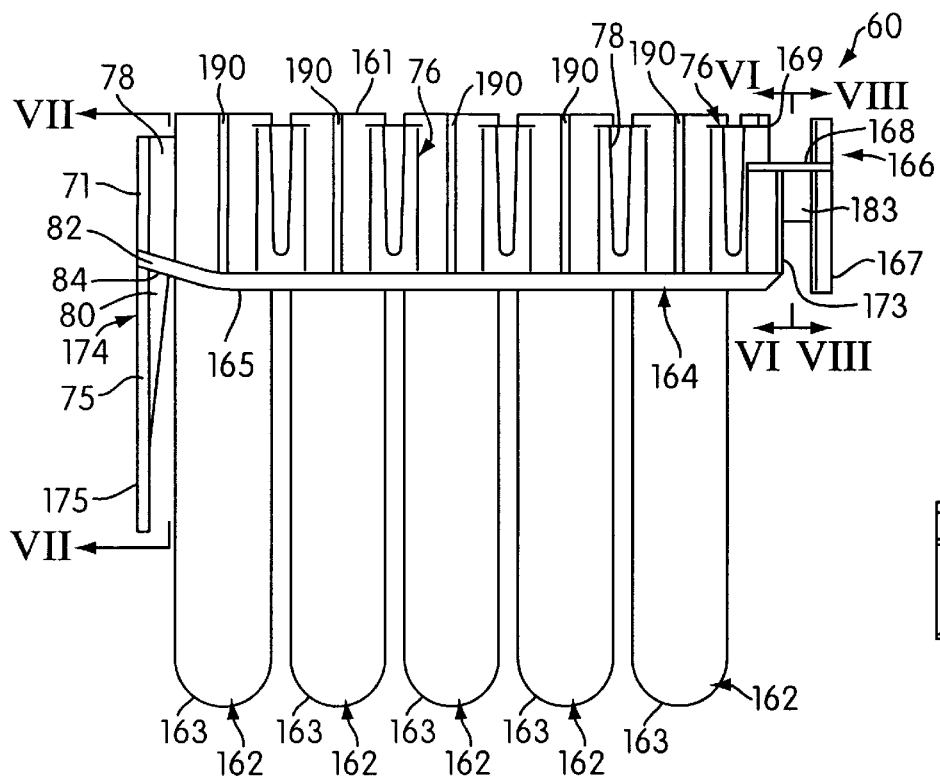
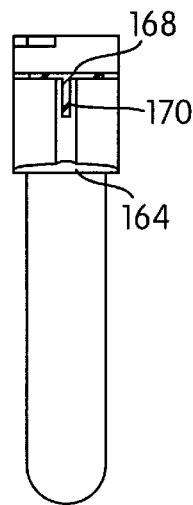
FIG. 6
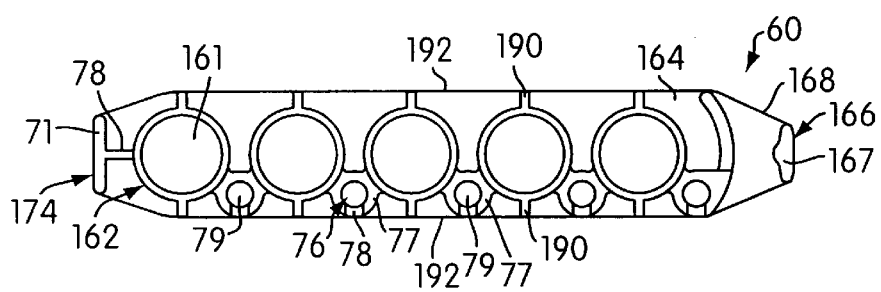
FIG. 5
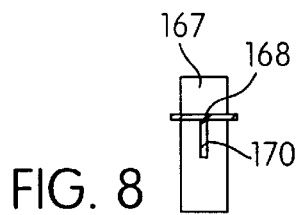
FIG. 8
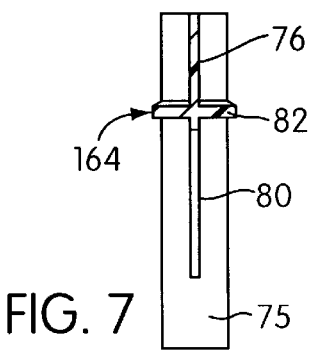
FIG. 7
FIG. 4

REACTION RECEPTACLE APPARATUS

This application claims the benefit of prior filed provisional application No. 60/046,800, filed May 2, 1997.

FIELD OF THE INVENTION

The present invention relates to reaction receptacles useful for containing chemical or biological substances.

BACKGROUND OF THE INVENTION

Reaction receptacles or test tubes are commonly used in the chemical and biological arts to perform a variety of types of assays in a contained space. Assays that commonly have one or more steps performed in reaction receptacles include chemical reactions, immunoassays, and nucleic acid-based assays. Examples of such reactions and assays are thoroughly described in the available literature and are well known to those skilled in the art. While reaction receptacles are generally manufactured and sold as individual units or test tubes, it is common for practitioners to use holding racks to conveniently and collectively organize a group of reaction receptacles for performing multiple assays simultaneously or sequentially. In some instances, multiple reaction receptacles are assembled as a unitary piece.

With most assays, a substance transfer device is used to dispense solutions into or remove solutions from reaction receptacles. The most familiar substance transfer devices are pipettes and aspirators including one or more tubular elements through which fluids are dispensed or withdrawn. When substance transfer devices are used in conducting a group of independent assays at about the same time or in close proximity to one another, there is always the concern that a substance transfer device will inadvertently serve as a vehicle in transferring substances or contaminants between reaction receptacles. An additional concern is that the practitioner will improperly add substances into or remove substances from a reaction receptacle. To minimize the risk of cross-contamination and pipetting and aspirating errors, practitioners must carefully monitor substance transfers and exercise nearly flawless precision when pipetting substances into or aspirating substances from reaction receptacles. Avoiding cross-contamination and pipetting and aspirating mistakes is particularly important when the assay is diagnostic in nature or is designed to provide information concerning the progress of a patient's disease over time or the success of a treatment regimen.

One way to limit opportunities for cross-contamination is to reduce the amount of surface area on the substance transfer device that can come into contact with the contents of a reaction receptacle. This objective can be achieved by using a contact-limiting element, such as a pipette tip, which essentially serves as a barrier between the outer surface of the pipette and the contents of a reaction receptacle. And by selecting a pipette tip of sufficient length and volume, contact between the pipette and contents of a reaction receptacle can be substantially eliminated. This is because substances from the reaction receptacle will be drawn into a portion of the pipette tip which falls below the bottom surface of the pipette. Of course, in most instances, it will also be important to have a single pipette tip dedicated to each reaction receptacle.

Where a number of pipette tips are used to perform multiple assays simultaneously or sequentially, practitioners typically need to position a supply of pipette tips at a location that can be conveniently accessed by at least one pipette. Providing a sufficient quantity of pipette tips becomes more complicated when the substance transfer device functions robotically in an automated (or partially automated) assay instrument. In an automated format, a large reserve of pipette tips may need to be placed in the instrument at a site that is accessible by the pipette, but which limits the total amount of space required. Accordingly, there is a need for pipette tips that are readily accessible by a robotic pipette without requiring the pipette to engage in complicated movements or to travel over substantial distances.

Another problem presented by conventional reaction receptacles is that they come packaged as individual test tubes that are not amenable to manipulation by an automated assay instrument. Individual reaction receptacles hinder throughput efficiency since the practitioner and instrument must each handle the reaction receptacles separately. And because conventional reaction receptacles are not provided with any structure that permits them to be manipulated by an automated instrument, reaction receptacles are generally stationed at one situs within the instrument and are not afforded any automated mobility. This lack of movement imposes certain architectural limitations and assay inefficiencies since the instrument must be designed around the positioning of the reaction receptacles. Accordingly, there is a need for a reaction receptacle apparatus which can be manipulated by an automated assay instrument, where the apparatus may include one reaction receptacle or plurality of reaction receptacles coupled together as a single operative unit.

SUMMARY OF THE INVENTION

It is an object of the present invention to provide a reaction receptacle apparatus that meets one or more of the needs set forth above. Thus, a reaction receptacle apparatus according to the present invention can be used to perform chemical or biological assays and comprises at least one reaction receptacle for containing substances used in performing such assays. When the reaction receptacle apparatus includes a plurality of reaction receptacles, the reaction receptacles are operatively coupled to one another, either directly or indirectly, and are capable of interacting with a substance transfer device that dispenses substances into or withdraws substances from some or all of the plurality of reaction receptacles making up the reaction receptacle apparatus.

So that the substance transfer device can safely and efficiently dispense substances into or withdraw substances from the reaction receptacles, one embodiment of the present invention provides for one or more contact-limiting elements associated with the reaction receptacle apparatus. The contact-limiting elements of this embodiment are constructed and arranged to be operatively engaged by the substance transfer device to limit potentially contaminating contact between at least a portion of the substance transfer device and a potentially contaminating substance that is dispensed into or withdrawn from a reaction receptacle by the substance transfer device. One or more contact-limiting elements are associated with each of one or more of the reaction receptacles of the reaction receptacle apparatus.

When the present invention includes contact-limiting elements, the reaction receptacle apparatus is outfitted with one or more contact-limiting element holding structures, each contact-limiting element holding structure being preferably associated with a different contact-limiting element. Each of the contact-limiting element holding structures is constructed and arranged to (i) receive and removably hold the associated contact-limiting element in an operative orientation in proximity to the associated receptacle so as to be operatively engageable by the substance transfer device, and (ii) allow the associated contact-limiting element to be removed from the associated contact-limiting element holding structure when the associated contact-limiting element is operatively engaged by the substance transfer device.

Because this embodiment of the reaction receptacle apparatus is supplied with its own contact-limiting elements, an automated assay instrument can be constructed so that the substance transfer device avoids complex motions and conveniently engages the contact-limiting elements when the reaction receptacle apparatus is brought into an operative position within the instrument. An additional benefit of this embodiment is that the instrument does not have to be configured to receive a store of contact-limiting elements, and practitioners are spared having to monitor the volume of contact-limiting elements in an instrument while assays are being run.

A further embodiment of the present invention is a reaction receptacle apparatus including receptacle apparatus manipulating structure to permit manipulation of the apparatus by an automated reaction receptacle manipulating device. According to this embodiment, the receptacle apparatus manipulating structure is constructed and arranged to be engaged by an automated reaction receptacle manipulating device, so that the reaction receptacle apparatus can be robotically manipulated within an automated instrument. The reaction receptacle apparatus of this embodiment includes at least one reaction receptacle and may optionally include the contact-limiting elements and associated contact-limiting element holding structures described above.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures. dr

BRIEF DESCRIPTION OF THE DRAWINGS

FIG. 4 is a side elevation of a first alternate embodiment of the reaction receptacle apparatus of the present invention;

FIG. 5 is a top view of the reaction receptacle apparatus of FIG. 4;

FIG. 6 is a cross-section in the direction "VI—VI" of FIG. 4;

FIG. 7 is a cross-section in the direction "VII—VII" in FIG. 4;

FIG. 8 is a cross-section in the direction "VIII—VIII" in FIG. 4;

DETAILED DESCRIPTION OF THE PREFERRED EMBODIMENT

Figure 1:
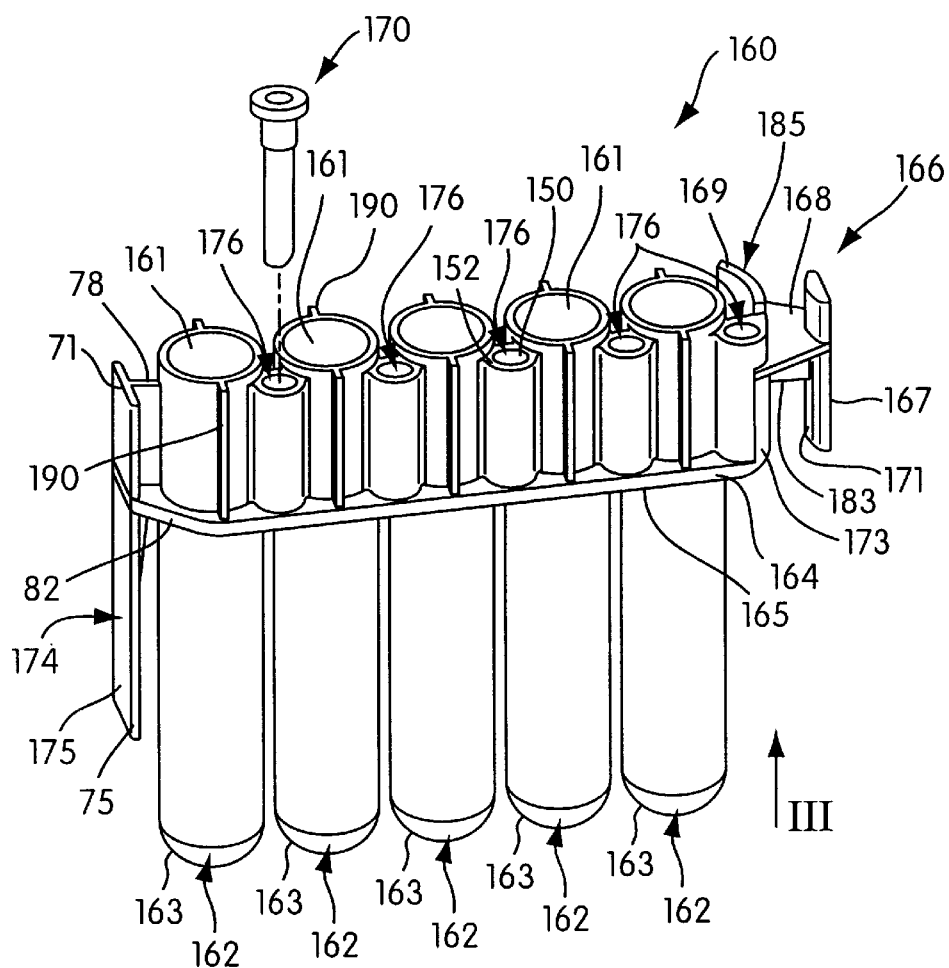
FIG. 1 is a perspective view of a first embodiment of a reaction receptacle apparatus and contact-limiting element in the form of a tiplet embodying aspects of the present invention.
Figure 3:
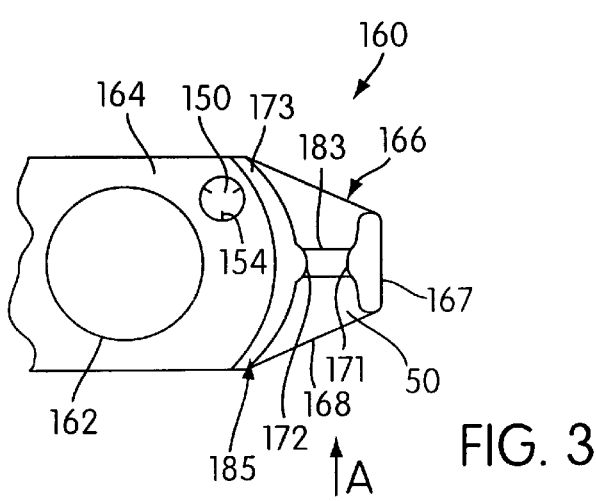
FIG. 3 is a partial bottom view of the reaction receptacle apparatus of FIG. 1 taken in the direction indicated by arrow "III" in FIG. 1.

As shown in FIGS. 1 and 3, a preferred embodiment of a reaction receptacle apparatus according to the present invention is designated generally by the reference character 160. As shown, the reaction receptacle apparatus 160 preferably comprises a plurality of individual receptacles 162. In the illustrated embodiment, the reaction receptacle apparatus 160 includes five individual receptacles 162, but a reaction receptacle according to the present invention may include any number of receptacles 162, as desired. Ten receptacles 162 are preferred and five receptacles 162 are most preferred. Each individual receptacle 162 preferably has a construction similar to that of a conventional test-tube, i.e., a cylindrical body with a circular open mouth 161 and a rounded closed bottom end 163. Each individual receptacle can, however, have other shapes, such as rectangular, octagonal, etc., and may have an upper end equipped with a closable lid structure or the like. Where the reaction receptacle includes a plurality of receptacles, the receptacles may have the same or different shapes and sizes. The receptacles 162 are preferably oriented in an aligned arrangement comprising a single row of receptacles 162 and are connected to one another by a connecting rib structure 164 which defines a downwardly facing shoulder 165 extending longitudinally along either side of the reaction receptacle apparatus 160. The receptacles 162 may be oriented in a different nonlinear arrangement, or a single reaction receptacle apparatus may comprise more than one row of receptacles 162.

Reaction receptacle apparatus 160 is preferably a single, integral piece formed of injection molded polypropylene. The most preferred polypropylene is sold by Montell Polyolefins, of Wilmington, Del., product number PD701NW. The Montell material is used because it is readily moldable and is chemically compatible with the preferred biological assays performed in the reaction receptacle apparatus. Moreover, the Montell material experiences a limited number of static discharge events, which is important when the results of the assay performed in the reaction receptacle apparatus are determined by the detection of light emitted by the contents of the apparatus at the conclusion of the assay. Static discharge events can interfere with accurate detection or quantification of the light output.

An arcuate shield structure 185 provided at one end of the reaction receptacle apparatus 160 includes an upper portion 169 and a lower portion 173. A receptacle apparatus manipulating structure 166, adapted to be engaged by a reaction receptacle manipulating device, extends from the shield upper portion 169. Receptacle apparatus manipulating structure 166 comprises a laterally extending plate 168 extending from shield upper portion 169 with a transverse piece 167 on the opposite end of the plate 168. A gusset wall 183 extends downwardly from lateral plate 168 between shield lower portion 173 and transverse piece 167.

As shown in FIG. 3, the shield lower portion 173 and transverse piece 167 have mutually facing convex surfaces. The reaction receptacle apparatus 160 is preferably engaged by manipulating devices and other components, as will be described below, by moving an engaging member of the manipulating device laterally (in the direction "A") into a space 50 between the shield lower portion 173 and the transverse piece 167. The convex surfaces of the shield lower portion 173 and transverse piece 167 provide for wider points of entry for an engaging member undergoing a lateral relative motion into the space 50. Vertically extending, raised arcuate ridges 171, 172 may be provided in the middle of the convex surfaces of the transverse piece 167 and shield lower portion 173, respectively. The purpose of ridges 171, 172 will be described below.

A label-receiving structure 174 provided on an end of the reaction receptacle apparatus 160 opposite receptacle apparatus manipulating structure 166 preferably includes an upper portion 71 and a lower portion 75, which together present a flat label-receiving surface 175. The label-receiving structure 174 further includes a vertical gusset wall 78 extending between upper portion 71 and the endmost receptacle 162 to provide a brace for the upper portion 71. As best shown in FIG. 4, a gusset wall 80 of the label-receiving structure 174 is oriented vertically and extends diagonally from a location proximate rib structure 164 toward a lower end of lower portion 75 to provide a brace for lower portion 75. Labels, such as machine-scannable bar codes, can be applied to the surface 175 to provide identifying and instructional information on the reaction receptacle apparatus 160. Labels can be applied to surface 175 by any suitable means, such as, printing them onto surface 175 or adhering a label sheet, by means of an adhesive, to surface 175.

Substances can be dispensed into or removed from the receptacles 162 through their open mouths 161 by means of a substance transfer device, such as a pipetting or aspirating apparatus (hereinafter referred to collectively as "pipetting apparatus" or "pipette"). The pipetting apparatus may include a slender tubular element (see, e.g., tubular element 220 in FIG. 11) that is inserted into the receptacle 162 through the open mouth 161 and which may come into contact with the receptacle 162 itself, the substance contained in the receptacle 162, and/or the substance being dispensed into the receptacle. A pipetting apparatus may be used to dispense substances into and/or remove substances from multiple individual receptacles 162. Accordingly, to reduce the likelihood of cross-contamination between individual receptacles 162, it is desirable to limit the amount of the pipetting apparatus that comes into contact with the substance or walls of any receptacle 162. Therefore, a contact-limiting element, which may take the form of a protective disposable tip, or tiplet, covers the end of the tubular element of the pipetting apparatus. One contact-limiting element is used to cover the end of the tubular element while the pipetting apparatus engages one individual receptacle to dispense substance into or withdraw substance from the receptacle. Before the pipetting apparatus moves to the next receptacle, that contact-limiting element is discarded or stored for later use with that receptacle, and a new contact-limiting element is engaged by the tubular element.

Figure 2:
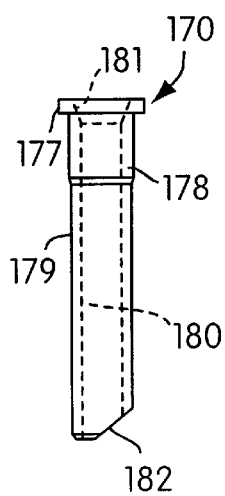
FIG. 2 is a side elevation of a contact-limiting tiplet.

As shown in FIG. 2, a preferred embodiment of a contact-limiting element comprises a tiplet 170. In the preferred embodiment, tiplet 170 comprises a tubular body 179 having a peripheral flange 177, preferably extending radially with respect to said tubular body 179, and a thickened wall portion 178, adjacent the peripheral flange 177, having a generally larger diameter than a remaining portion of the tubular body 179 of the tiplet 170. An axially extending inner bore 180 passes through the tiplet 170. Bore 180 includes an outwardly flared end 181, which facilitates insertion of a bottom free end of a tubular element of a pipetting apparatus into the bore 180 of tiplet 170. The inner diameter of inner bore 180 provides an interference fit with the outer diameter of the tubular element to frictionally secure tiplet 170 onto the tubular element when the bottom end of the tubular element is forced into the inner bore 180.

In the illustrated embodiment, the tubular body 179 and inner bore 180 are generally cylindrical in shape, consistent with the typically cylindrical shape of the tubular element of a substance transfer device, such as a pipetting or aspirating device. The present invention is not limited, however, to contact-limiting elements having tubular bodies and inner bores that are cylindrical, as the tubular body and inner bore of the contact-limiting element may have a shape that is other than cylindrical to conform to non-cylindrical tubular elements of substance transfer devices.

The bottom end of the tiplet 170 preferably includes a beveled portion 182. When tiplet 170 is used on the bottom of the tubular element of a pipetting apparatus used for aspirating substances from a receptacle 162, the beveled portion 182 will prevent a vacuum from forming between the end of the tiplet 170 and the bottom 163 of the receptacle 162.

Figure 17:
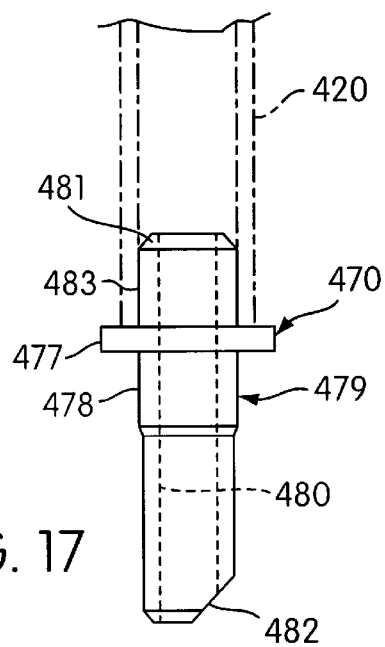
FIG. 17 is a side elevation of an alternate embodiment of a contact-limiting tiplet engaged by a tubular element of a substance transfer device.

An alternate embodiment of a contact-limiting element is a tiplet designated by reference number 470 in FIG. 17. Tiplet 470 comprises a tubular body 479 having a peripheral flange 477, preferably extending radially with respect to said tubular body 479, and a thickened wall portion 478, adjacent the peripheral flange 477, of generally larger diameter than a remaining portion of the tubular body 479 of the tiplet 470. An axially extending inner bore 480 passes through the tiplet 470. Bore 480 includes a bevelled end 481, which facilitates insertion of an upper end 483 of the tubular body 479 into a bottom free end of a tubular element 420. The outer diameter of upper end 483 of the tubular body 479 provides an interference fit with the inner diameter of the tubular element 420 to frictionally secure tiplet 470 onto the tubular element 420 when the upper end 483 of the tubular body 479 is inserted into the bottom free end of the tubular element 420.

Again, the tubular body 479 and inner bore 480 need not necessarily be generally cylindrical in shape, as illustrated in FIG. 17, may have a shape that is other than cylindrical to conform to non-cylindrical tubular elements of substance transfer devices.

The bottom end of the tiplet 470 preferably includes a beveled portion 482. When tiplet 470 is used on the bottom of the tubular element of a pipetting apparatus used for aspirating substances from a receptacle 162, the beveled portion 482 will prevent a vacuum from forming between the end of the tiplet 470 and the bottom 163 of the receptacle 162.

As shown in FIG. 1, the reaction receptacle apparatus 160 preferably includes contact-limiting element holding structures in the form of tiplet holding structures 176 adjacent the open mouth 161 of each respective receptacle 162. Each tiplet holding structure 176 provides an elongated orifice 150, preferably generally cylindrical in shape, within which is received a contact-limiting tiplet 170 (470). An annular end face 152 extends about the orifice 150, and when the tiplet 170 (470) is inserted into a tiplet holding structure 176, the peripheral flange 177 (477) contacts the end face 152 of tiplet holding structure 176 to limit the depth to which the tiplet 170 (470) can be inserted into the orifice 150. The outside diameter of the thickened wall portion 178 (478) is slightly larger than inside diameter of the orifice 150. Alternatively, and preferably, a plurality of small, raised ribs 154 (see FIG. 3) extend longitudinally along the inner wall of the orifice 150 at different circumferentially-spaced positions. The crests of the raised ribs 154 define an inner diameter that is slightly smaller than the outer diameter of the thickened wall portion 178 (478). Accordingly, the tiplet holding structure 176 provides a sliding interference fit between the thickened wall portion 178 (478) and the inner diameter of the orifice 150 or between the thickened wall portion 178 (478) and the crests of the ribs 154. Thus, tiplet 170 (470) is held securely within the orifice 150 of the tiplet holding structure 176 so the tiplet 170 (470) is unlikely to dislodge from the tiplet holding structure 176, even if the reaction receptacle apparatus 160 is inverted. On the other hand, if the tiplet 170 (470) is frictionally engaged by the tubular element of a pipetting apparatus while the tiplet 170 (470) is held in the tiplet holding structure 176, the frictional hold between the tiplet 170 (470) and the tubular element is greater than the frictional hold between the tiplet 170 (470) and the tiplet holding structure 176. Thus, the tiplet 170 (470) should remain secured on the end of the tubular element when the tubular element is withdrawn in an axial direction from the orifice 150 of the tiplet holding structure 176.

Throughout the remainder of this specification, reference will be made only to tiplet 170 (the embodiment shown in FIG. 2). Those skilled in the art, however, will appreciate that the following descriptions and illustrations can apply to tiplet 470 (the embodiment shown in FIG. 17) as well.

An alternate tiplet holding structure 76 is shown in FIGS. 4 and 5. Reaction receptacle apparatus 60 includes a tiplet holding structure 76 that is different from the tiplet holding structure 176 of reaction receptacle apparatus 160 of FIG. 1. In all other respects, however, reaction receptacle apparatus 60 is identical to reaction receptacle apparatus 160. Tiplet holding structure 76 includes a tiplet-receiving orifice 79 with an end face 77 surrounding orifice 79 and forming a partial annulus. A slot 78 extends longitudinally along a wall of the tiplet holding structure 76. Slot 78 allows the tiplet holding structure 76 to expand when a tiplet 170 is inserted into the tiplet holding structure 76, and the resiliency of the material of which the reaction receptacle apparatus 60 is formed provides a frictional fit between a tiplet 170 and the tiplet holding structure 76.

As shown in FIGS. 1, 4, and 5, connecting rib structure 164 extends along both sides of the reaction receptacle apparatus 160 and defines downwardly facing shoulders 165 with outer edges 192 along each side of the reaction receptacle apparatus 160 (60). The reaction receptacle apparatus 160 (60) is operatively supported within a diagnostic instrument or the like by means of the shoulders 165 resting on parallel, horizontal flanges spaced apart from one another by a distance slightly greater than the width of the individual receptacle 162, but less than the width of the rib structure 164 between edges 192. Such flanges may be defined by a slot extending from an edge of a reaction receptacle apparatus supporting plate. In an automated instrument for processing the contents of a reaction receptacle apparatus, the reaction receptacle apparatus may be inserted into and removed from a supporting structure by a reaction receptacle apparatus manipulating device.

At an end of the rib structure 164 opposite the receptacle apparatus manipulating structure 166, two upwardly angled portions 82 provide upwardly angled shoulders 84 on both sides of the reaction receptacle apparatus 160 (60). The upwardly angled shoulders 84 facilitate sliding of the reaction receptacle apparatus 160 (60) onto a supporting structure.

Figure 9:
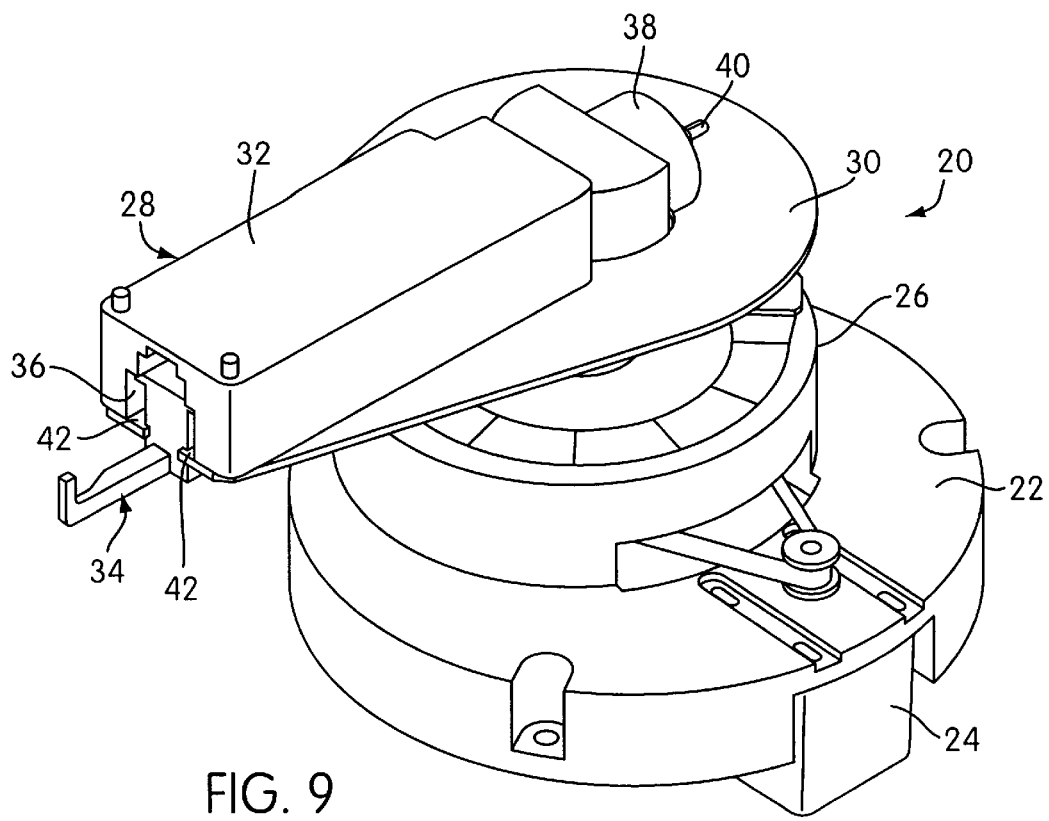
FIG. 9 is a perspective view of an exemplary reaction receptacle apparatus manipulating device for manipulating a reaction receptacle apparatus according to the present invention.
Figure 10:
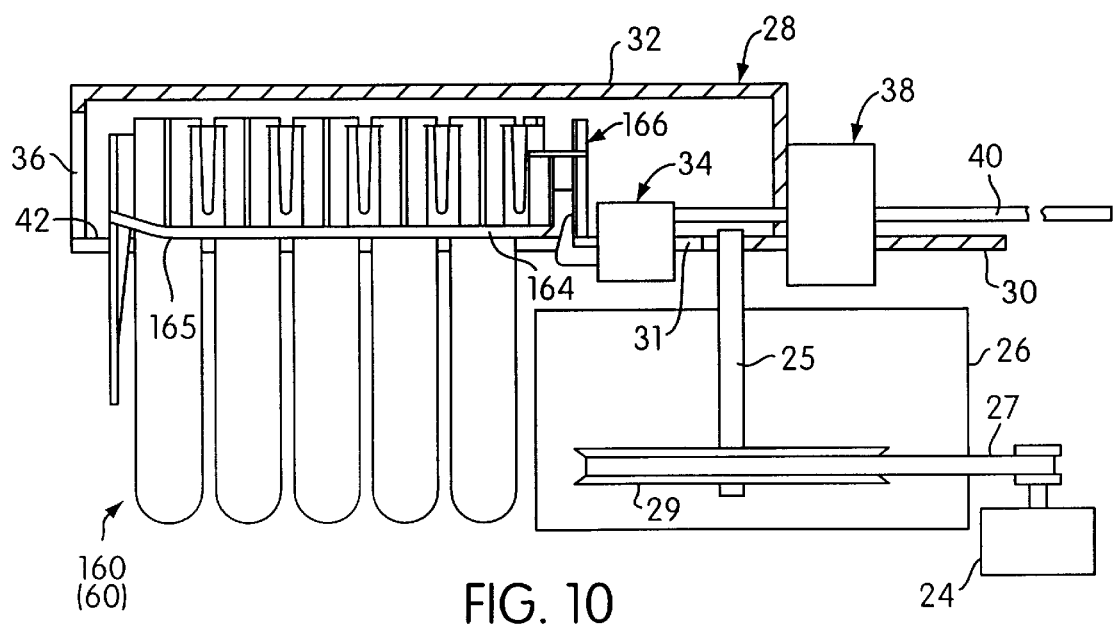
FIG. 10 is a side elevation, partially in cross-section, of the manipulating device of FIG. 9 with a reaction receptacle apparatus resident therein.

An exemplary device 20 for manipulating a reaction receptacle apparatus 160 (60) is shown in FIGS. 9 and 10. The device 20 includes a base structure 22 attached to a mounting bracket or mounting plate of an instrument which processes the contents of numerous reaction receptacle apparatuses according to the present invention and may perform one or more assays within each reaction receptacle apparatus 160. The manipulating device 20 moves the reaction receptacle apparatuses from one location to another within the instrument.

The manipulating device 20 further includes a rotating transport carrier 28 which rotates about a shaft 25 by means of a stepper motor 24 which turns a pulley 29 attached to the shaft 25 via a drive belt 27. The shaft 25 and pulley 29 may be covered by a pulley housing 26. The rotating transport carrier 28 includes a base plate 30 covered by a housing 32. The housing 32 includes an opening 36 at one end thereof, and the base plate 30 includes a slot 31 formed therein. A manipulating hook 34 is mounted for sliding translation in the slot 31 and is attached to a threaded drive screw 40 that is actuated by a stepper motor 38 to extend and retract the manipulating hook 34 within the slot 31.

To engage the receptacle apparatus manipulating structure 166 of the reaction receptacle apparatus 160, the manipulating hook 34 is extended to a forward position projecting from the opening 36 as shown in FIG. 9. A lateral translation of the manipulating hook 34 is effected, such as by effecting a small rotation of the rotating transport carrier 28, to place the manipulating hook 34 in the space 50 between the lower portion 173 of the arcuate shield structure 185 and the transverse piece 167 of the receptacle apparatus manipulating structure 166. With the manipulating structure 166 engaged, the stepper motor 38 retracts the drive screw 40, pulling the manipulating hook 34 and the reaction receptacle apparatus 160 back into the rotating transport carrier 28. The downwardly facing shoulders 165 defined by the connecting rib structure 164 of the reaction receptacle apparatus 160 are supported by the base plate 30 along opposite edges 42 of the slot 31, thus supporting the reaction receptacle apparatus 160 in the rotating transport carrier 28. With the reaction receptacle apparatus 160 secured within the rotating transport carrier 28, the carrier 28 can be rotated by the stepper motor 24 to a different position at which the stepper motor 38 can extend the drive screw 40 and the manipulating hook 34 to push the reaction receptacle apparatus 160 out of the rotating transport carrier 28 and into a different location within the instrument.

Figure 11:
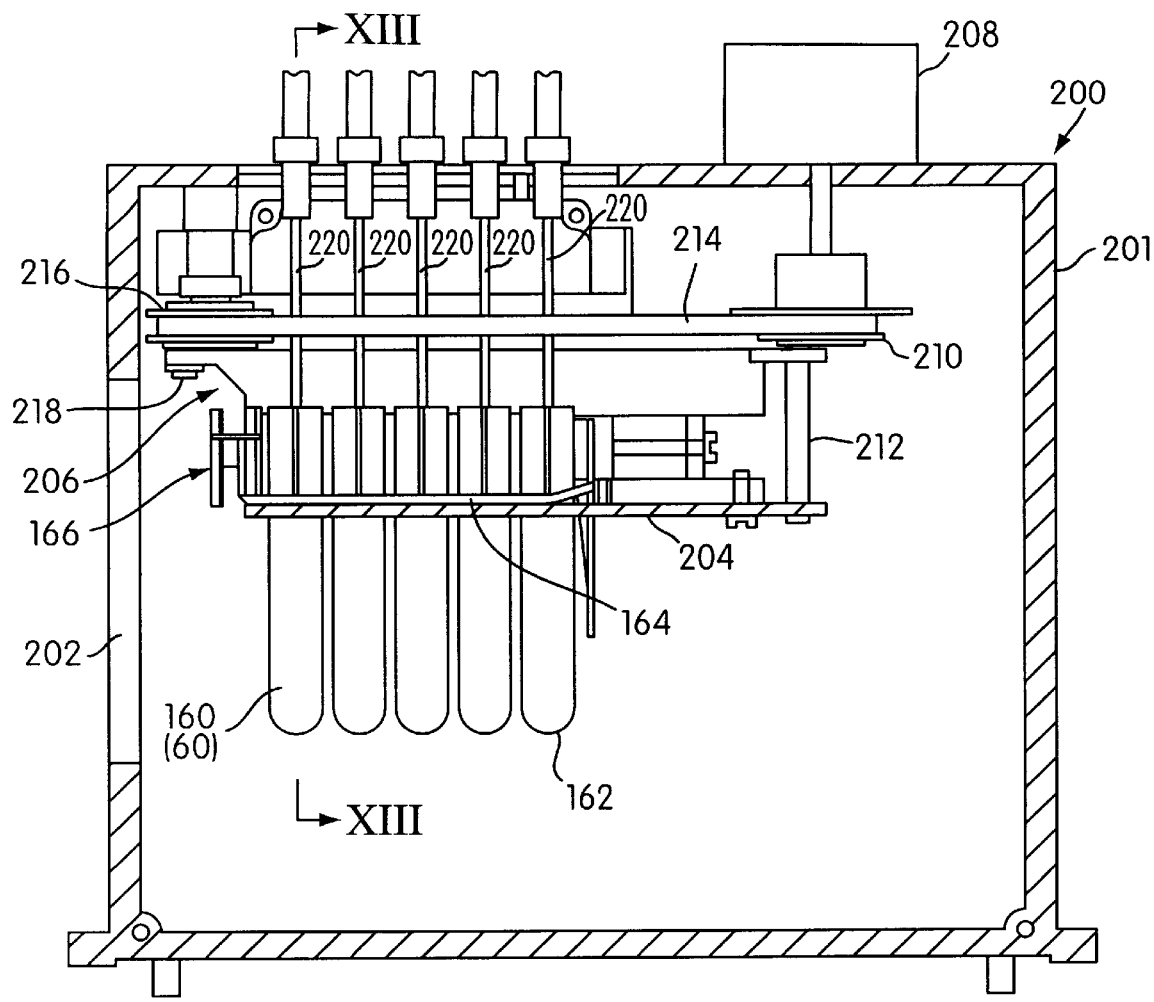
FIG. 11 is a side elevation, partially in cross-section, of an exemplary reaction receptacle apparatus processing device for processing a reaction receptacle apparatus according to the present invention.

An exemplary reaction receptacle processing device 200 is shown in FIG. 11. Processing device 200 may represent one of many similar or related devices which together make up a reaction receptacle processing instrument.

The processing device 200 includes a housing 201 with an opening 202 formed therein. A reaction receptacle apparatus 160 can be inserted into the processing device 200 through the opening 202 and removed through the opening 202 by a manipulating device such as the manipulating device 20 shown in FIGS. 9 and 10 and described above. Inside the housing 201 the reaction receptacle apparatus is supported by a receptacle carrier structure 206 having a base plate 204 (see also FIGS. 13 and 14) with a receptacle receiving slot (not shown) formed therein so that the reaction receptacle apparatus 160 can be supported by means of portions of the plate 204 along opposite edges of the slot supporting the connecting rib structure 164 of the reaction receptacle apparatus 160.

Processing device 200 may be a mixing device for mixing the contents of the reaction receptacle apparatus 160; the processing device 200 may be a dispensing device for simultaneously dispensing substance into each of the individual receptacles 162 of the reaction receptacle apparatus 160; or the processing device 200 may be a device for simultaneously aspirating substance from each of the receptacles 162 of the reaction receptacle apparatus 160. Alternatively, the processing device 200 may perform any combination of two or more of the above functions.

As a mixing device, the receptacle carrier structure 206 may be coupled to an orbital mixing assembly comprising a stepper motor 208, a drive wheel 210 with an eccentric pin 212 extending therefrom, and an idler wheel 216 having an eccentric pin 218 and being coupled to the drive wheel 210 by means of a belt 214. As the stepper motor 208 rotates the drive pulley 210 which in turn rotates the idler pulley 216, the eccentric pins 212 and 218 engage the receptacle carrier structure 206 thus moving the receptacle carrier structure and the reaction receptacle apparatus 160 carried thereby in an orbital path of motion. Movement at a sufficiently high frequency can cause sufficient agitation of the reaction receptacle apparatus 160 to mix the contents thereof.

Figure 13:
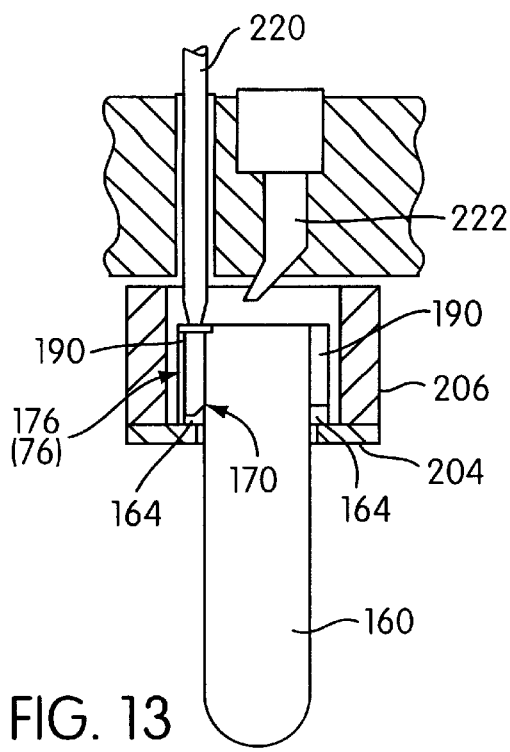
FIG. 13 is a cross-section showing a reaction receptacle apparatus according to the present invention carried by a receptacle carrier structure within a receptacle apparatus processing device with a tubular element of the processing device engaging a contact-limiting tiplet disposed within a contact-limiting holding structure of the apparatus of the present invention.
Figure 14:
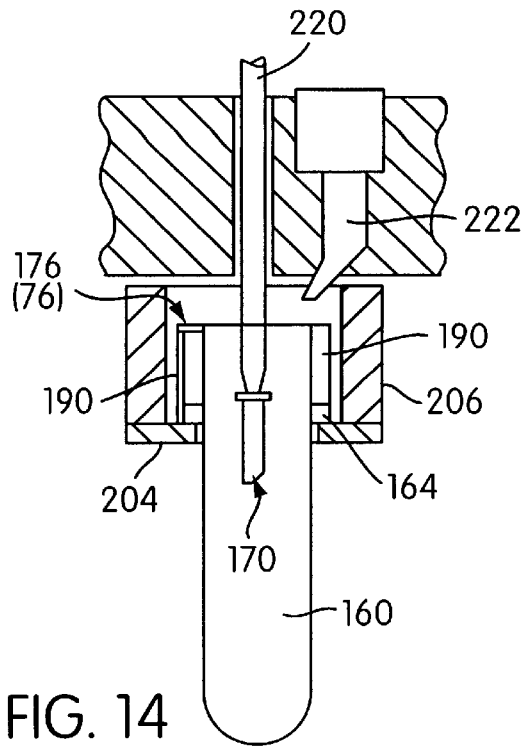
FIG. 14 is a cross-section showing the reaction receptacle apparatus disposed within the receptacle carrier structure with the tubular elements and the contact-limiting tiplet disposed on the end of the tubular element inserted into the apparatus.

As shown in FIGS. 1, 4, and 5, lateral ribs 190 extend longitudinally along the outer walls of the receptacles 162 above the connecting rib structure 164 at diametrically opposed positions with respect to one another. The outer edges of the lateral ribs 190 are generally co-planar with the outer edges 192 of the connecting rib structure 164. The lateral ribs provide additional strength and rigidity to the open mouth 161 of the receptacle 162. In addition, the outer edges of the lateral ribs 190 can engage the sidewalls of a receptacle carrier structure 206, as shown in FIGS. 13 and 14, to limit the extent to which the reaction receptacle apparatus 160 will be allowed to tilt laterally within the receptacle carrier structure 206. Although it is generally preferred that lateral ribs 190 be provided on each of the receptacles 162, lateral ribs 190, when included, can be provided on less than all of the receptacles 162 as well.

When presented in the receptacle carrier structure 206, the reaction receptacle apparatus 160 can be engaged by a dispensing and/or aspirating system comprising an array of tubular elements 220. The dispensing and/or aspirating system preferably includes five tubular elements 220 oriented so as to correspond to the orientations of the individual receptacles 162 of the reaction receptacle apparatus 160. The tubular elements 220 are coupled to means for providing vertical movement of the free ends of the tubular elements 220 with respect to the reaction receptacle apparatus 160 to move the ends of the tubular elements 220 into and out of the individual receptacles 162 to aspirate and/or dispense substances. In addition, tubular elements 220 are coupled to means, such as a fluid pump and fluid source or a vacuum pump, for delivering fluid to each of the tubular elements 220 or providing a suction at each of the tubular elements 220.

As described above, however, before the tubular elements 220 are inserted into the reaction receptacles 162, it is preferred that a contact-limiting tiplet 170 be placed on the end of each tubular element 220. Accordingly, the tubular elements 220 are first lowered to simultaneously engage all of the tiplets 170 carried in their respective tiplet holding structures 176. The array of tubular elements 220 can be coupled to means for providing lateral translation of the tubular elements 220 for moving the tubular elements 220 to a position above the tiplet holding structures 176. Alternatively, the receptacle carrier structure 206 itself can be moved laterally to place the tiplet holding structures 176 below the respective tubular elements 220. Where the receptacle carrier structure 206 is coupled to an orbital mixing assembly as described above, the stepper motor 208 can move the assembly a limited number of steps, thus moving the receptacle carrier structure 206 and the reaction receptacle apparatus 160 a portion of one orbital path to place the tiplet holding structures 176 below the tubular elements 220 as shown in FIG. 13.

As shown in FIGS. 1, 4, and 5, each of the respective tiplet holding structures 176 (76) is preferably disposed at a position between adjacent receptacles 162. Locating the tiplet holding structures 176 (76) between the adjacent receptacles 162 places the tubular elements 220 on the orbital paths of the contact-limiting element holding structures 176 (76) as the reaction receptacle apparatus 160 is moved with respect to the pipettes 220. Thus, the orbital mixer assembly can be used to properly position the tiplet holding structures 176 (76) with respect to the tubular elements 220, as described above. In addition, placing the tiplet holding structures 176 (76) between adjacent receptacles 162 provides for a narrower profile of the reaction receptacle apparatus 160 (60) than if the tiplet holding structures 176 (76) were located on the outer portion of the receptacles 162 nearest the edge 192 of the connecting rib structure 164.

The processing device 200 may also include an array of fixed nozzles 222 for dispensing substances into the receptacles 162 of the reaction receptacle apparatus 160 held in the receptacle carrier structure 206.

Figure 12:
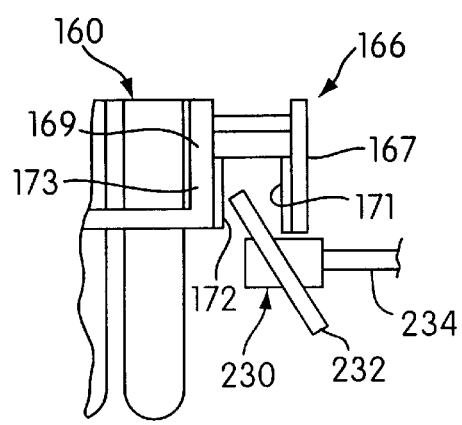
FIG. 12 is a partial side view of a reaction receptacle apparatus according to the present invention and a skewed wobbler plate for imparting an oscillatory vibration to the apparatus.

As shown in FIG. 12, an alternate, oscillating mixing device 230 comprises a skewed wobbler plate 232 disposed on a shaft 234 driven by a motor (not shown). The reaction receptacle apparatus 160, carried by a carrier structure (not shown), is moved with respect to the oscillating mixing device 230—or the oscillating mixing 230 is moved with respect to the reaction receptacle apparatus 160—until the wobbler plate 232 is disposed in the space 50 between the lower portion 173 of the arcuate shield structure 185 and the transverse piece 167 of the receptacle apparatus manipulating structure 166. As the shaft 234 rotates, the position of the portion of the wobbler plate 232 engaged with the receptacle apparatus 160 varies in a linearly oscillating manner to impart a linear oscillating motion to the reaction receptacle apparatus 160.

The raised ridges 171, 172 provided in the middle of the convex surfaces of the transverse piece 167 and the lower portion 173, respectively, can minimize the surface contact between the wobbler plate 232 and the convex surfaces, thus limiting friction therebetween. It has been determined, however, that raised ridges 171, 172 can interfere with the engagement of the manipulating hook 34 of a manipulating device 20 with the apparatus manipulating structure 166. Therefore, raised ridges 171, 172 are preferably omitted.

Figure 15:
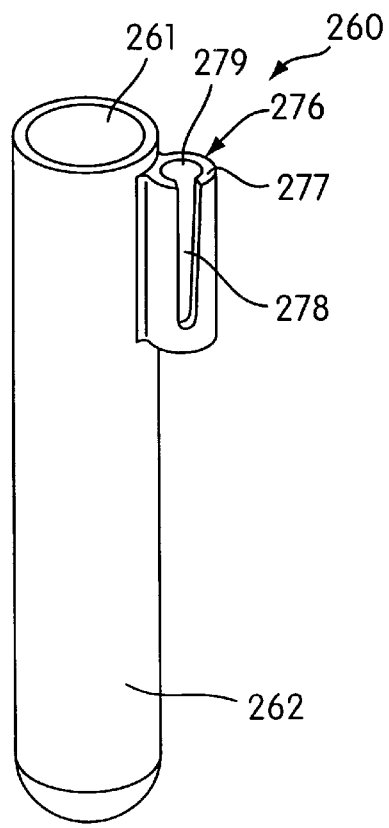
FIG. 15 is a perspective view of a second alternate embodiment of a reaction receptacle apparatus of the present invention.

In the preferred embodiment of the reaction receptacle apparatus of the present invention, a linear array of individual receptacles 162 are integrally coupled together by the connecting rib structure 164. The broadest aspects of the present invention, however, contemplate a reaction receptacle apparatus 260, as shown in FIG. 15, which comprises a single receptacle 262 having an open-mouth 261 and a connected contact-limiting element holding structure, such as tiplet holding structure 276, attached to the receptacle 262. In the embodiment illustrated in FIG. 15, tiplet holding structure 276 includes a tiplet receiving orifice 279, a longitudinal slot 278, and an end-face 277 forming a portion of an annulus. Alternatively, the contact-limiting element holding structure may be in the form of tiplet holding structure 176 of FIG. 1, in which no longitudinal slot is formed therein and in which a plurality of longitudinally extending raised ribs 154 (see FIG. 3) are formed on the inner surface of the orifice 150.

Figure 16:
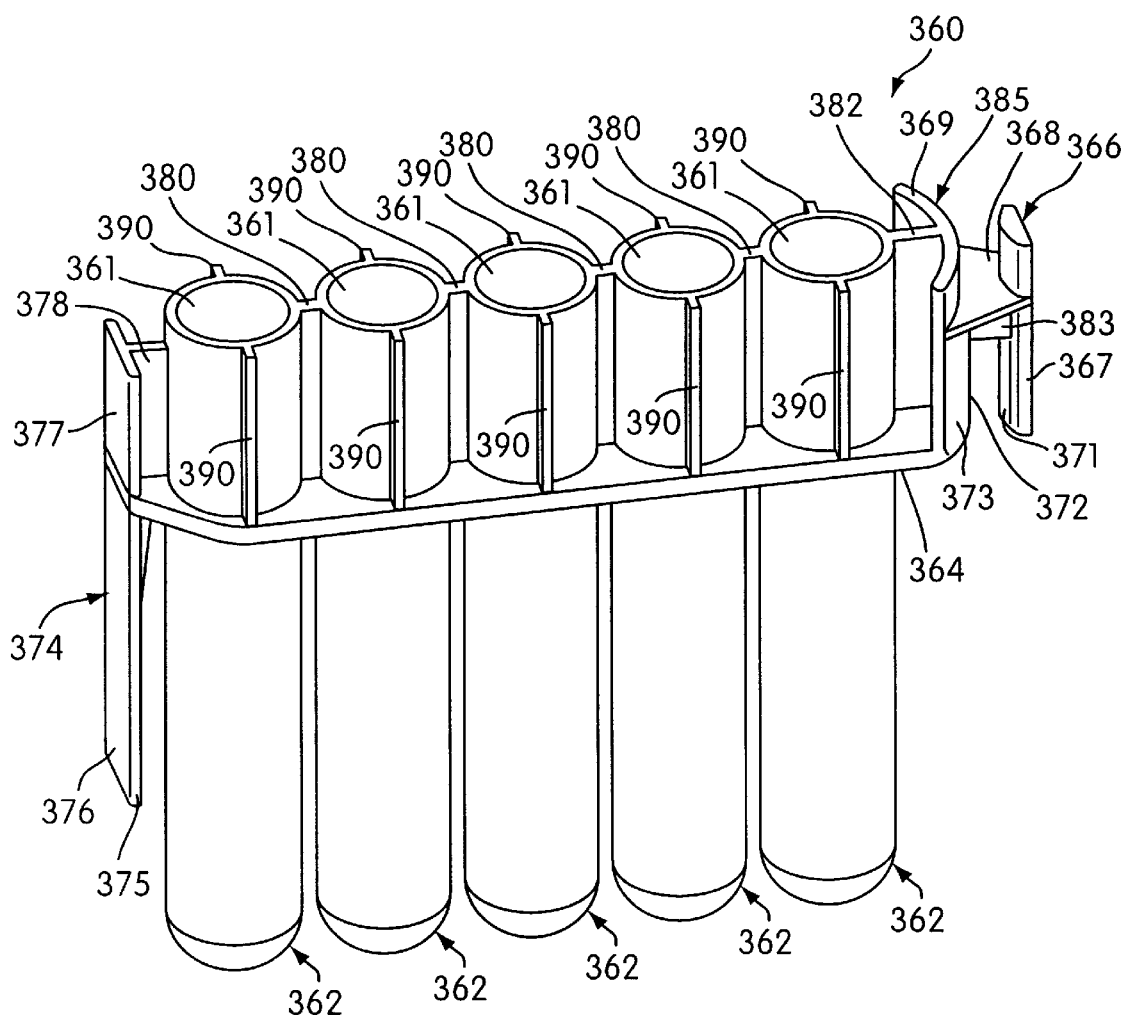
FIG. 16 is a perspective view of a third alternate embodiment of a reaction receptacle apparatus of the present invention.

A further alternate embodiment of the reaction receptacle apparatus of the present invention is generally designated by reference number 360 in FIG. 16. As shown in the drawing, the preferred embodiment of reaction receptacle apparatus 360 includes a plurality of individual receptacles 362, each having an open receptacle mouth 361. The most preferred embodiment of the reaction receptacle apparatus 360 includes five individual receptacles 362. Individual receptacles 362 are connected to one another by a connecting rib structure 364.

Reaction receptacle apparatus 360 is in most respects identical to the reaction receptacle apparatuses described above and shown in FIGS. 1, 4, and 5, except that reaction receptacle apparatus 360 does not include contact-limiting holding structures 176 (76) associated with each individual receptacle 362. Nor does reaction receptacle apparatus 360 include a contact-limiting element, such as tiplet 170, associated with each individual receptacle 362.

Reaction receptacle apparatus 360 also preferably includes a label-receiving structure 374 having an upper portion 377 and a lower portion 375 cooperating so as to define a flat label-receiving surface 376. A vertical gusset wall 378 extends between the upper portion 377 of label-receiving structure 374 and the outer wall of the endmost individual receptacle 362.

In addition, reaction receptacle apparatus 360 includes an arcuate shield structure 385 having an upper portion 369 and a lower portion 373. A receptacle apparatus manipulating structure 366 includes a transverse piece 367 connected to the arcuate shield structure 385 by means of a plate 368 extending between upper portion 369 of arcuate shield structure 385 and transverse piece 367, and a gusset wall 383 extending between the lower portion 373 of the arcuate shield structure 385 and the transverse piece 367 of the receptacle apparatus manipulating structure 366. As with the previous embodiments, the transverse piece 367 and the lower portion 373 of the arcuate shield structure 385 preferably have mutually-facing convex surfaces, and the surfaces may include vertical arcuate ridges 371 and 372, respectively. The receptacle apparatus manipulating structure 366 and the arcuate ridges 371 and 372 of the reaction receptacle apparatus 360 serve the same function as the receptacle apparatus manipulating structure 166 and the raised arcuate ribs 171 and 172 described above.

The reaction receptacle apparatus 360 may further include connecting walls 380 extending between adjacent individual receptacles 362 at upper portions thereof above the connecting rib structure 364. In addition, a gusset wall 382 may be provided between the endmost individual receptacle 362 and the arcuate shield structure 385. Finally, the reaction receptacle apparatus 360 may further include lateral ribs 390 extending vertically along the outer surfaces of diametrically opposed positions of upper portions of the individual receptacles 362. The lateral ridges 390 of the reaction receptacle apparatus 360 serve the same function as do the lateral ribs 190 described above.

While the invention has been described in connection with what is presently considered to be the most practical and preferred embodiments, it is to be understood that the invention is not to be limited to the disclosed embodiments, but, on the contrary, it is intended to cover various modifications and equivalent arrangements included within the spirit and scope of the appended claims. Thus, it is to be understood that variations in the particular parameters used in defining the present invention can be made without departing from the novel aspects of this invention as defined in the following claims.

What is claimed is:

1. A receptacle apparatus for use in performing chemical or biological assays comprising:

a row of two or more longitudinally-spaced receptacles for containing one or more substances, said receptacles being capable of interacting with a substance transfer device constructed and arranged to dispense substances into or withdraw substances from one or more receptacles of said plurality of receptacles;

a connecting rib structure fixedly connected to and extending away from outer surfaces of said receptacles and along said row of receptacles, said connecting rib structure defining generally straight edge surfaces extending along opposite sides of said row of receptacles and having generally flat shoulders facing toward bottom ends of said receptacles;

one or more contact-limiting elements associated with each of said receptacles, each of said contact-limiting elements being constructed and arranged to be operatively engaged by the substance transfer device to limit contact between at least a portion of the substance transfer device and substances dispensed into or withdrawn from said receptacles by the substance transfer device; and one or more contact-limiting element holding structures associated with each of said receptacles and attached to an outer surface thereof, each said contact-limiting element holding structure being associated with one of said contact-limiting elements, and each said contact-limiting element holding structure being constructed and arranged to:

receive and removably hold said associated contact-limiting element in an operative orientation in proximity to said associated receptacle, to permit said contact-limiting element to be operatively engaged by the substance transfer device, and allow said associated contact-limiting element to be removed from said associated contact-limiting element holding structure when said associated contact-limiting element is operatively engaged by the substance transfer device.

2. The receptacle apparatus of claim 1 wherein said receptacles are arranged so as to be simultaneously engageable by the substance transfer device to permit the substance transfer device to dispense substances into or withdraw substances from each of said receptacles simultaneously.

3. The receptacle apparatus of claim 1 comprising five of said receptacles.

4. The receptacle apparatus of claim 1 wherein one end of said connecting rib structure is bent upwardly along opposite sides of said row of receptacles to define upwardly sloped edge surfaces extending from said generally straight edge surfaces.

5. The receptacle apparatus of claim 1 further comprising a receptacle apparatus manipulating structure coupled to said row of receptacles, said receptacle apparatus manipulating structure being constructed and arranged to be engaged by a receptacle apparatus manipulating device to manipulate said receptacle apparatus.

6. The receptacle apparatus of claim 1 further comprising a label-receiving structure coupled to said row of receptacles and presenting a label-receiving surface for affixing human and/or machine readable information thereto.

7. The receptacle apparatus of claim 1 wherein at least one of said receptacles has ribs extending outwardly from opposed outer surfaces thereof, said opposed outer surfaces corresponding to said opposite sides of said row of receptacles.

8. The receptacle apparatus of claim 1, wherein said receptacles and said connecting rib structure form a single piece.

9. The receptacle apparatus of claim 8, wherein said single piece consists of polypropylene.

10. The receptacle apparatus of claim 1, each of said receptacles including a generally cylindrical hollow structure with a circular open upper end and a closed bottom end.

11. The receptacle apparatus of claim 1, wherein each of said one or more contact-limiting elements comprises a protective tiplet comprising:

a tubular body having a proximal end and a distal end and an inner bore formed in said tubular body from said proximal end to said distal end; and a peripheral flange disposed about an outer periphery of said tubular body, said protective tiplet being constructed and arranged to be frictionally secured onto a free end of a tubular element of the substance transfer device when said protective tiplet is engaged by the tubular element.

12. The receptacle apparatus of claim 11, wherein a portion of said inner bore is sized to receive the free end of the tubular element inserted into said inner bore and to provide an interference fit between an inner surface of said tubular body and an outer surface of the free end of the tubular element when the tubular element is inserted into said inner bore.

13. The receptacle apparatus of claim 11, wherein said tubular body is sized to be inserted into the free end of the tubular element and to provide an interference fit between an outer surface of said tubular body and an inner surface of the free end of the tubular element when said tubular body is inserted into the tubular element.

14. The receptacle apparatus of claim 11, wherein said tubular body and said inner bore of said protective tiplet are generally cylindrical in shape.

15. The receptacle apparatus of claim 11, wherein a portion of said tubular body proximate said distal end is formed at an angle with respect to a longitudinal axis of said tubular body.

16. The receptacle apparatus of claim 11, wherein said protective tiplet further comprises structure extending for a longitudinal extent along said tubular body from said peripheral flange and defining an outside diameter larger than an outside diameter of a remaining portion of said tubular body.

17. The receptacle apparatus of claim 11, wherein each of said one or more contact-limiting element holding structures comprises a tiplet holding structure, said tiplet holding structure having an elongated orifice formed therein for receiving the tubular body of an associated protective tiplet inserted into said elongated orifice and a peripheral end face oriented transversely to an axis of said elongated orifice and surrounding an end of said elongated orifice, wherein said peripheral flange of said protective tiplet is in contact with said peripheral end face of said tiplet holding structure when said tubular body of said protective tiplet is fully inserted into said elongated orifice, said tiplet holding structure being constructed and arranged to provide a sliding interference fit between said elongated orifice and said tubular body of said associated protective tiplet inserted into said elongated orifice, whereby said associated protective tiplet is frictionally secured within said elongated orifice.

18. The receptacle apparatus of claim 17, further comprising a slot formed in said tiplet holding structure and extending along a side of said elongated orifice, said slot being constructed and arranged to permit said tiplet holding structure to elastically expand when said protective tiplet is inserted into said elongated orifice.

19. The receptacle apparatus of claim 17, wherein said tubular body and said inner bore of said protective tiplet are generally cylindrical in shape and said elongated orifice is generally cylindrical in shape, and wherein said tiplet holding structure further comprises a plurality of circumferentially spaced, axially extending raised ribs formed on an inner surface of said elongated orifice, wherein an inside diameter defined by crests of said plurality of raised ribs is smaller than an outside diameter of a portion of said tubular body of said associated protective tiplet inserted into said elongated orifice to provide the sliding interference fit between the crests of said plurality of raised ribs and said tubular body of said associated protective tiplet.

20. The receptacle apparatus of claim 19, wherein said tubular body of said protective tiplet includes a thickened wall portion along an extent of said tubular body, said thickened wall portion having an outside diameter that is greater than an outside diameter of a remaining portion of said tubular body, and wherein the inside diameter defined by the crests of said plurality of raised ribs is smaller than the outside diameter of said thickened wall portion of said tubular body of said associated protective tiplet inserted into said elongated orifice to provide the sliding interference fit between the crests of said plurality of raised ribs and said thickened wall portion of said tubular body of said associated protective tiplet.

21. The receptacle apparatus of claim 1, further comprising a shield structure disposed at one end of said receptacle apparatus and a receptacle manipulating structure attached to said shield structure, said receptacle manipulating structure including a lateral plate extending from said shield structure and a transverse piece attached to an end of said lateral plate opposite said shield structure and extending transversely with respect thereto, said receptacle manipulating structure being constructed and arranged to be engaged by a receptacle apparatus manipulating device by positioning a manipulating hook of said receptacle apparatus manipulating device into a space between said shield structure and said transverse piece to manipulate said receptacle apparatus.

22. The receptacle apparatus of claim 21, wherein said shield structure and said transverse piece include mutually facing convex surfaces on opposite sides of said space between said shield structure and said transverse piece.

23. The receptacle apparatus of claim 22, further comprising raised ribs, one disposed on each of said mutually facing convex surfaces, each rib extending axially with respect to a curvature of each said convex surface and being disposed generally in the middle of each said convex surface.

24. A reaction receptacle apparatus comprising:
   a row of two or more longitudinally-spaced, generally cylindrical receptacles, each said receptacle having an open top and a closed bottom, wherein said receptacles are generally parallel to one another;
   a connecting rib structure fixedly connected to and extending away from outer surfaces of said receptacles and along said row of receptacles, said connecting rib structure defining generally straight edge surfaces extending along opposite sides of said row of receptacles and having generally flat shoulders facing toward bottom ends of said receptacles;
   a protective tip associated with each of said receptacles for covering a distal end of a tubular element used for introducing reaction material into or removing reaction material from said associated receptacle, said protective tip comprising:
      a tubular body having a proximal end, a distal end, and an inner bore formed through said tubular body from said proximal end to said distal end; and
      a peripheral flange formed about a perimeter of said tubular body; and
   a protective tip holding structure associated with each of said receptacles and attached to an outer surface thereof, said protective tip holding structure comprising a tubular structure fixedly disposed proximate said open end of said associated receptacle and extending generally parallel to said associated receptacle and having a generally cylindrical orifice formed therein which defines an inside diameter, said tubular structure defining an end surface about a periphery of an entrance to said generally cylindrical orifice, wherein said tubular structure of said protective tip holding structure is adapted to receive and frictionally hold said tubular body of said protective tip, said peripheral flange of said protective tip engaging said end surface of said tubular structure when said tubular body of said protective tip is fully inserted into said generally cylindrical orifice of said protective tip holding structure.

25. The reaction receptacle apparatus of claim 24 comprising five of said receptacles.

26. The reaction receptacle apparatus of claim 24, wherein one end of said connecting rib structure is bent upwardly along opposite sides of said row of receptacles to define upwardly sloped edge surfaces extending from said generally straight edge surfaces.

27. The reaction receptacle apparatus of claim 24 further comprising receptacle apparatus manipulating structure coupled to said row of receptacles, said receptacle apparatus manipulating structure being constructed and arranged to be engaged by a reaction receptacle apparatus manipulating device to manipulate said reaction receptacle apparatus.

28. The reaction receptacle apparatus of claim 24 further comprising a label-receiving structure coupled to said row of receptacles and presenting a label-receiving surface for affixing human and/or machine readable information thereto.

29. The reaction receptacle apparatus of claim 24 wherein at least one of said receptacles has ribs extending outwardly from diametrically opposed outer surfaces thereof, said diametrically opposed surfaces corresponding to said opposite sides of said row of receptacles.

30. The reaction receptacle apparatus of claim 24, wherein said receptacles and said connecting rib structure form a single piece.

31. The reaction receptacle apparatus of claim 30, wherein said single piece consists of polypropylene.

32. The reaction receptacle apparatus of claim 24, wherein a portion of said tubular body proximate said distal end is formed at an angle with respect to a longitudinal axis thereof.

33. The reaction receptacle apparatus of claim 24, wherein said tubular body of said protective tip is generally cylindrical in shape and includes a thickened wall portion along an extent of said tubular body, said thickened wall portion defining an outside diameter larger than an outside diameter of a remaining portion of said tubular body.

34. The reaction receptacle apparatus of claim 24, further comprising a slot formed in said tip holding structure and extending along a side of said generally cylindrical orifice, said slot being constructed and arranged to permit said tip holding structure to elastically expand when said tubular body of said protective tip is inserted into said generally cylindrical orifice.

35. The reaction receptacle apparatus of claim 24, wherein said tubular body is generally cylindrical in shape and wherein said tip holding structure further comprises a plurality of circumferentially spaced, axially extending raised ribs formed on an inner surface of said generally cylindrical orifice, an inside diameter defined by crests of said plurality of circumferentially spaced raised ribs being smaller than an outside diameter of a portion of said tubular body of said protective tip inserted into said generally cylindrical orifice.

36. The reaction receptacle apparatus of claim 35, wherein said tubular body of said protective tip includes a thickened wall portion along an extent of said tubular body, said thickened wall portion defining an outside diameter that is larger than the inside diameter defined by the crests of said plurality of circumferentially spaced raised ribs.

37. The reaction receptacle apparatus of claim 24, further comprising a shield structure disposed at one end of said reaction receptacle apparatus and a receptacle apparatus manipulating structure attached to said shield structure, said receptacle apparatus manipulating structure including a lateral plate extending from said shield structure and a transverse piece attached to an end of said lateral plate opposite said shield structure and extending transversely with respect thereto, said receptacle apparatus manipulating structure being constructed and arranged to be engaged by a reaction receptacle apparatus manipulating device by positioning a manipulating hook of said reaction receptacle manipulating device into a space between said shield structure and said transverse piece to manipulate said reaction receptacle apparatus.

38. The reaction receptacle apparatus of claim 37, wherein said shield structure and said transverse piece include mutually facing convex surfaces on opposite sides of said space between said shield structure and said transverse piece.

39. The reaction receptacle apparatus of claim 38, further comprising raised ribs, one disposed on each of said mutually facing convex surfaces, each rib extending axially with respect to a curvature of each said convex surface and being disposed generally in the middle of each said convex surface.

\* \* \* \* \*